United States Patent [19]

Serimian et al.

[11] Patent Number: Plant 6,541

[45] Date of Patent: Jan. 17, 1989

[54] NECTARINE TREE, SUMMER LION—TREE

[76] Inventors: Donald M. Serimian, 2961 McCall Ave.; Lionel M. Serimian, 11310 E. Manning, both of Selma, Calif. 93662

[21] Appl. No.: 120,495

[22] Filed: Nov. 13, 1987

[51] Int. Cl.[4] ..... A01H 5/00
[52] U.S. Cl. ..... Plt./41
[58] Field of Search ..... Plt./41

*Primary Examiner*—Robert E. Bagwill
*Attorney, Agent, or Firm*—Worrel & Worrel

[57] ABSTRACT

A new and distinct variety of nectarine tree denominated varietally as "Summer Lion—Three" which is somewhat similar to the Red Lion Nectarine Tree (U.S. Plant Pat. No. 5,591) and the May Grand Nectarine Tree (U.S. Plant Pat. No. 2,794) with which it is most closely related but which is distinguished therefrom and characterized as to novelty by producing fruit which are mature for commercial harvesting approximately July 25 through August 5 in Fresno County, Calif. and which further produces fruit that has a large size, a yellow-colored firm flesh, and is freestone by nature.

1 Drawing Sheet

BACKGROUND OF THE NEW VARIETY

The present invention relates to a new and distinct variety of nectarine tree, hereinafter referred to as "Summer Lion—Three", and more particularly to such a nectarine tree which is somewhat similar in physical characteristics to the May Grand Nectarine Tree (U.S. Plant Pat. No. 2,794), and the Red Lion Nectarine Tree (U.S. Plant Pat. No. 5,591), from which it was derived as a progeny following the successful cross pollination of the two nectarine tree varieties noted above, but from which it is distinguished therefrom and characterized as to novelty in producing fruit which mature for commercial harvesting approximately July 25 through August 5 in the San Joaquin Valley of central California; the subject variety maturing approximately six weeks later than the May Grand Nectarine Tree (U.S. Plant Pat. No. 2,794) and approximately fifteen days earlier than the Red Lion Nectarine Tree (U.S. Plant Pat. No. 5,591); and which is otherwise distinguishable by producing fruit which have a dark, intense red skin coloration, and are large in size as compared with other nectarine cultivars maturing in approximately the same season.

A substantial portion of the applicants' professional lives has been devoted to the creation and marketing of new and distinct varieties of fruit trees. The instant variety resulted from such activities. In this regard, the applicants have regularly selected fruit trees having desirable characteristics and thereafter cross pollinated the selected fruit trees in an effort to produce progeny having improved characteristics. For example, in the creation of the instant variety of nectarine tree, an object of the present invention was to perpetuate the superior characteristics of the Red Lion Nectarine Tree (U.S. Plant Pat. No. 5,591) and the desirable characteristics of the May Grand Nectarine Tree (U.S. Plant Pat. No. 2,794).

ORIGIN AND ASEXUAL REPRODUCTION OF THE NEW VARIETY

The applicants cross pollinated a May Grand Nectarine Tree (U.S. Plant Pat. No. 2,794), and a Red Lion Nectarine Tree (U.S. Plant Pat. No. 5,591) in a test block which is situated on the applicant's ranch, the ranch being located at 11024 East Dinuba Avenue in Selma, Calif. in the County of Fresno, in early 1983.

The resultant progeny were grown to a state sufficiently mature to determine that the characteristics were desirable. The instant variety was thereafter selected and asexually reproduced by the applicants by removing scion wood which was subsequently budded into test nectarine trees in the fall of 1984. This first asexual reproduction has been continually observed by the applicants and it has been determined that the characteristics of these offspring were identical to those of the original nectarine tree.

BRIEF DESCRIPTION OF THE DRAWINGS

The accompanying drawing is a color photograph of four mature fruit of the subject variety; a twig bearing typical leaves displaying the dorsal and ventral coloration thereof; two fruit showing their external coloration sufficiently mature for harvesting and shipment; and two fruit divided in the axial plane to illustrate the flesh coloration; along with two stones, all of the subject variety.

DETAILED DESCRIPTION

Referring more specifically to the pomological details of this new and distinct variety of nectarine tree, the following has been observed under the ecological conditions prevailing at the applicants' orchard which is situated in Fresno County, Calif. All major color code designations are by reference to the Dictionary of Color, by Maerz and Paul, Second Edition, published in 1950. Common color names are also used occasionally.

TREE

Size:

*Generally.*—Average.

Form: Upright, to upright — spreading in form. The form of the subject variety is determined by pruning practices.

Vigor: Medium. The instant variety is hardy when grown under typical San Joaquin Valley ecological conditions.

Trunk:

*Diameter.*—Average.

*Texture.*—Moderately rough.

Bark color: Gray-brown, (7-E-9).

Trunk — lenticels: Numerous moderately large corky type lenticels are evident.

Trunk — scarf skin: A moderate amount of scarf skin is present on the bark surface.

Branches:

*Size.*—Average.

*Surface texture.*—Medium.

*Color.*—Brown (6-A-9).

Immature branches:

*Color.*—Light green (19-H-2).

*Texture.*—Smooth.

LEAVES

Size:

*Generally.*—Large.

*Average length.*—19.3 cm.

*Average width.*—4.7 cm.

Leaf form: Lanceolate, with a sharp acuminate tip. The leaf tip may appear slightly twisted.

Color:

*Dorsal surface.*—Dark green, (23-J-7).

*Ventral surface.*—Gray-green, (21-H-5).

*Leaf mid-vein.*—Yellow-green, (17-H-2) when viewed from the ventral surface of the leaf.

Leaf mid-vein:

*Thickness.*—Approximately 1 mm. when measured at the center portion of the leaf.

Marginal form: Crenate, occasionally moderately coarse, regular in appearance. The leaf margins are moderately undulate.

Leaf petiole:

*Size.*—Medium.

*Length.*—Approximately 12 to 14 mm.

*Thickness.*—Approximately 1.5 mm.

*Color.*—Yellow-green, (17-G-30); the petiole groove is a somewhat slightly darker green, (19-F-4).

Leaf glands:

*Size.*—Average to above average.

*Form.*—Mixed, the variety having both reniform and globose types.

*Numbers.*—Variable, from two to five glands are present. As a general matter, two or three leaf glands are present on the leaf petiole just below the basal leaf margin. One or two more leaf glands, in this instance, a reniform type, are present on the basal leaf margin.

*Pattern.*—Usually alternate.

*Color.*—Young glands have a shiny yellow-green appearance, (17K-3); the glands darken and deteriorate with advancing age.

Stipules:

*Numbers.*—Usually two.

*Position.*—Subtending the base of the leaf petiole.

*Length.*—Approximately 8 to 9 mm.

*Marginal form.*—Serrate.

*Color.*—Green-yellow (17-I-5); the stipule color darkens with advancing maturity. The variety is early deciduous.

FLOWERS

Generally

The flowers of the subject variety are not particularly distinctive.

Blooming time:

*Generally.*—Mid-season to slightly late in relation to other common nectarine varieties growing in this geographical area of California.

Flower size:

*Generally.*—Large, showy form.

Bloom amount: Average.

Flower buds and scales: Pubescent and average in size.

Bud form: Conic. The variety usually produces one to two flower buds per node.

Petals:

*Size.*—Large.

*Form.*—Ovate.

*Color.*—A light pink (1-E-2). The petals of the subject variety darken with advancing maturity.

Pedicle:

*Length.*—Very short.

Pedicle color: Green, (19-K-5).

Nectaries:

*Color.*—Orange, (11-J-11). This part of the plant darkens with age.

Anthers:

*Size.*—Small.

Stamens:

*Length.*—Average. Although in most instances the stamens are shorter than the pistil.

Pistil:

*Color.*—A light yellow-green, (17-H-3). The pistil is usually positioned above the anthers when fully extended.

*Texture.*—Glabrous.

FRUIT

Maturity when described: Ripe for commercial harvesting and shipment approximately July 25, 1987 through Aug. 5, 1987.

Size:

*Generally.*—Uniform and very large.

*Average diameter in the cheek plane.*—Approximately 79 to 82 mm.

*Average diameter in the suture plane.*—Approximately 74 to 80 mm.

*Average diameter in the axial plane.*—Approximately 78 to 83 mm.

Form: Moderately asymmetrical, with one-half of the fruit generally larger than the other half.

Shape: Ovate to nearly oval in its lateral aspect. Nearly globose in its apical aspect. In some instances, the ventral suture of the subject variety is moderately prominent.

Suture:

*Generally.*—The suture of the subject variety appears as a very shallow depression which extends from the base to the apex. The suture of the subject variety further appears more distinct over the apical shoulder area ventrally.

*Color.*—The suture color usually is quite similar to the underlying blush or ground color. Some fine, thin, and dark red stripes occasionally appear along the suture area (8-L-8). This coloration is usually more evident over the basal shoulder area.

*Form.*—A moderate depression occurs along the suture line and is further evident in the immediate vicinity, and on both sides of the apex.

Ventral surface:

*Form.*—Smooth and rounded, moderately lipped on both sides of the fruit in the area of the apical shoulders. Occasionally, some fruit display a low prominence at mid-suture.

Stem cavity:

*Generally.*—Moderately deep, and narrow.

*Stem indentation.*—Some stem indentation is evident in the cavity shoulder.

*Form.*—Slightly oval.

*Width.*—Approximately 31 to 35 mm.

*Length.*—Approximately 32 to 35 mm.

*Depth.*—Approximately 16 to 17 mm.

Base:

*Position.*—Variable, from a right angle to slightly oblique with respect to the fruit axis.

*Form.*—Moderately truncate.

Apex:

*Shape.*—Rounded with a low tip. The apex, in most instances, is higher at the apical shoulders.

Pistil point:

*Position.*—Apical. Moderately depressed areas subtend the apex on both the ventral and dorsal suture lines.

Stem:

*Length.*—Approximately 11 to 12 mm.

*Thickness.*—Average, approximately 3½ to 4 mm.

*Color.*—Olive green, (20-J-4).

Skin:

*Thickness.*—Average.

*Texture.*—Glabrous.

*Flavor.*—Mild.

Tenacious to flesh: Yes.

Tendency to crack: Not observed.

Skin:

*Color.*—Generally — the blush color covers approximately 80% to 95% of the fruit surface. In most instances, the only ground color evident is that portion of the skin which is pressed next to a branch where the subject fruit was attached.

Blush color: Variable, a deep mahogany red to a bright cherry red (8-L-8) to (5-L-10), respectively. Some intermediate red color may be evident. The blush color is often overlain with dark red mottling which is variable with respect to its hue. The density of the mottling is noteworthy in the basal shoulder area but is not exclusively limited thereto.

Flesh color: At commercial maturity, the flesh color is a uniform yellow-amber (10-J-5). The pit cavity is stained a dark red (7-L-9). The dark stain extends approximately 4 to 5 mm. into the flesh.

Pit cavity:

*Texture.*—A moderate amount of callous is present in the pit cavity.

Flesh texture:

*Generally.*—Firm and crisp at commercial maturity. The subject variety becomes melting and juicy with advancing maturity.

Flesh fibers:

*Numbers.*—Numerous.

*Texture.*—Medium.

*Color.*—Light.

Ripening: Even.

Flavor: Very good, rich and well balanced.

Aroma: Moderate, pleasant.

Overall eating quality: Superior.

STONE

Attachment: Completely freestone; a few fibers may occasionally cling to the basal area of the stone.

Stone size:

*Generally.*—Large.

*Average length.*—Approximately 38 to 40 mm.

*Average width.*—Approximately 25 to 27 mm.

*Average thickness.*—19 to 22 mm.

Fibers:

*Numbers.*—Few.

*Length.*—Moderately long.

Form: Obovate, occasionally strongly so.

Stone base:

*Shape.*—Truncate.

*Position.*—The base angle is variable with respect to the fruit axis; both right angle and oblique forms are evident.

Hilum:

*Size.*—Large and well defined.

*Form.*—Oval, with the tapered end situated on the dorsal suture edge.

Apex:

*Shape.*—Pointed with sharp acuminate tip.

Sides:

*Shape.*—Usually unequal, at times strongly so.

Stone surface:

*Texture.*—Moderately rough, with deep grooves appearing laterally over the apical shoulder. The stone surface has formed therein deep and often irregularly shaped pits which appear over lateral and mid-stone surfaces. Shallow and fine ridges are evident over the basal shoulders, these ridges converge basally.

Ventral edge:

*Width.*—Moderately wide.

*Wings.*—Multiple low wings occur from the base to the apex. A central wing is slightly more prominent in the basal shoulder area.

Dorsal edge:

*Width.*—Moderately wide.

*Texture.*—Coarse with high discontinuous ridges which subtend to a medium depth groove that extends from the base to mid-stone; the dorsal suture is slightly eroded over the apical shoulders.

Stone color:

*Dry.*—Variable from dark brown to a lighter brown, (7-C-10 to 13-E-9). Violet staining is considerable over the basal areas.

Tendency to split: Not observed.

Fruit use: Fresh market and dessert type nectarine for both local and long distance shipping.

Keeping quality: Good.

Shipping quality: Unknown, although the firm, crisp flesh at commercial maturity strongly indicates that the subject variety will have noteworthy shipping characteristics.

Although the new variety of nectarine tree possesses the described characteristics as a result of the growing conditions prevailing in the San Joaquin Valley of central California, it is to be understood that variations of the usual magnitude and characteristics incident to growing conditions, fertilization, pruning and pest control are to be expected.

Having thus described and illustrated our new variety of nectarine tree, what we claim is:

1. A new and distinct variety of nectarine tree to be denominated varietally as "Summer Lion—Three" substantially as illustrated and described and which is characterized principally as to novelty by its production of dark red fruit which are ripe for commercial harvesting approximately July 25 through August 5 in Selma, Calif., the fruit of the subject variety being further characterized as to novelty by having a large size, a superior shape, and being freestone by nature.

* * * * *

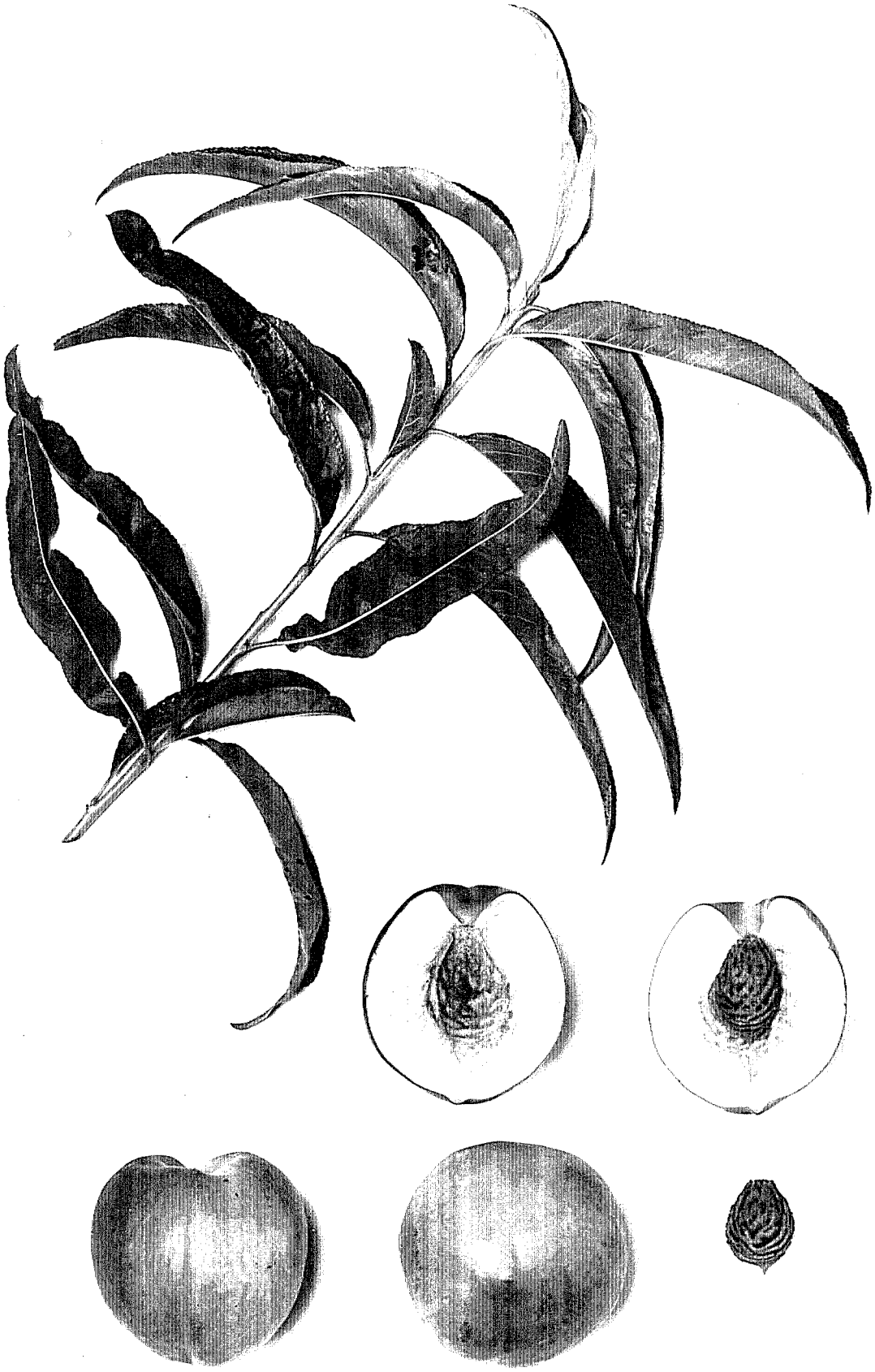

UNITED STATES PATENT AND TRADEMARK OFFICE

CERTIFICATE OF CORRECTION

PATENT NO. :PP 6,541

DATED : February 17, 1989

INVENTOR(S) : Lionel M. Serimian and Donald M. Serimian

It is certified that error appears in the above-identified patent and that said Letters Patent is hereby corrected as shown below:

In the title

Delete "NECTARINE TREE, "SUMMER LION - TREE""

Insert ---NECTARINE TREE, "SUMMER LION - THREE"

Signed and Sealed this

Twentieth Day of June, 1989

*Attest:*

DONALD J. QUIGG

*Attesting Officer*

*Commissioner of Patents and Trademarks*